US008070794B2

(12) United States Patent
Issenmann

(10) Patent No.: US 8,070,794 B2

(45) Date of Patent: Dec. 6, 2011

(54) FRANGIBLE BRIDGE STRUCTURE FOR A STENT, AND STENT INCLUDING SUCH BRIDGE STRUCTURES

(75) Inventor: Gonzague Issenmann, Clichy (FR)

(73) Assignee: Stentys S.A.S., Paris (FR)

(*) Notice: Subject to any disclaimer, the term of this patent is extended or adjusted under 35 U.S.C. 154(b) by 261 days.

(21) Appl. No.: 12/448,771

(22) PCT Filed: Jan. 8, 2008

(86) PCT No.: PCT/IB2008/000025

§ 371 (c)(1), (2), (4) Date: Jul. 7, 2009

(87) PCT Pub. No.: WO2008/084376

PCT Pub. Date: Jul. 17, 2008

(65) Prior Publication Data

US 2010/0057190 A1 Mar. 4, 2010

Related U.S. Application Data

(60) Provisional application No. 60/880,418, filed on Jan. 16, 2007.

(30) Foreign Application Priority Data

Jan. 9, 2007 (FR) ...................................... 07 00109

(51) Int. Cl.
*A61F 2/06* (2006.01)

(52) U.S. Cl. ...................................................... 623/1.15

(58) Field of Classification Search ................. 623/1.11, 623/1.12, 1.13, 1.14, 1.15, 1.16, 1.18, 1.19, 623/1.2, 1.21

See application file for complete search history.

(56) References Cited

U.S. PATENT DOCUMENTS

| | | | |
|---|---|---|---|
| 5,104,404 | A | 4/1992 | Wolff |
| 5,514,154 | A | 5/1996 | Lau et al. |
| 5,545,210 | A | 8/1996 | Hess et al. |
| 5,749,825 | A | 5/1998 | Fischell et al. |
| 5,766,237 | A | 6/1998 | Cragg |
| 5,769,817 | A | 6/1998 | Burgmeier |
| 5,827,321 | A | 10/1998 | Roubin et al. |
| 5,911,754 | A | 6/1999 | Kanesaka et al. |
| 6,017,362 | A | 1/2000 | Lau |
| 6,066,167 | A | 5/2000 | Lau et al. |
| 6,068,655 | A | 5/2000 | Sequin et al. |
| 6,129,755 | A | 10/2000 | Mathis et al. |
| 6,187,034 | B1 | 2/2001 | Frantzen |
| 6,258,117 | B1 | 7/2001 | Camrud et al. |
| 6,342,067 | B1 | 1/2002 | Mathis et al. |

(Continued)

FOREIGN PATENT DOCUMENTS

| | | | |
|---|---|---|---|
| AU | 200151922 | A1 | 8/2001 |

(Continued)

*Primary Examiner* — S. Thomas Hughes
*Assistant Examiner* — Jonathan W Miles
(74) *Attorney, Agent, or Firm* — Oliff & Berridge, PLC

(57) ABSTRACT

A frangible bridge structure for a stent includes three successive branches, a first of which is connected to one of the stent portions which the bridge structure makes it possible to connect and a second of which is connected to the other of the stent portions which the bridge structure makes it possible to connect, these first and second branches being connected, by two connecting portions, to a third intermediate branch, between the first and second branches, these three branches extending parallel to each other with the longitudinal direction of these branches preferably being oriented perpendicular to the longitudinal direction of the stent, and in immediate proximity to each other.

33 Claims, 4 Drawing Sheets

2 7 7 6 6 3 7 2 6 7 7 100 7 7 6 7 7 6 6 7 7 4 15 15

U.S. PATENT DOCUMENTS 6,348,065 B1 2/2002 Brown et al.
6,409,754 B1 6/2002 Smith et al.
6,464,720 B2 10/2002 Boatman et al.
6,478,816 B1 11/2002 Kveen et al.
6,485,510 B1 11/2002 Camrud et al.
6,485,511 B2 11/2002 Lau et al.
6,533,807 B2 3/2003 Wolinsky et al.
6,562,067 B2 5/2003 Mathis
6,596,022 B2 7/2003 Lau et al.
6,602,281 B1 8/2003 Klein
6,602,282 B1 8/2003 Yan
6,652,579 B1 11/2003 Cox et al.
6,666,883 B1 12/2003 Seguin et al.
6,679,910 B1 1/2004 Granada
6,699,280 B2 3/2004 Camrud et al.
6,706,061 B1 3/2004 Fischell et al.
6,796,999 B2 9/2004 Pinchasik
6,881,223 B2 4/2005 Penn et al.
6,887,264 B2 5/2005 Penn et al.
6,908,479 B2 6/2005 Lau et al.
6,916,336 B2 7/2005 Patel et al.
6,949,120 B2 9/2005 Kveen et al.
7,029,492 B1 4/2006 Mitsudou et al.
2001/0037146 A1 11/2001 Lau et al.
2001/0037147 A1 11/2001 Lau et al.
2001/0041930 A1 11/2001 Globerman et al.
2001/0044648 A1 11/2001 Wolinsky et al.
2001/0056298 A1 12/2001 Brown et al.
2002/0107560 A1 8/2002 Richter
2003/0050688 A1 3/2003 Fischell et al.
2003/0078649 A1 4/2003 Camrud et al.
2003/0083731 A1 5/2003 Kramer et al.
2003/0114912 A1 6/2003 Sequin et al.
2003/0125791 A1 7/2003 Sequin et al.
2003/0135266 A1 7/2003 Chew et al.
2003/0139796 A1 7/2003 Sequin et al.
2003/0139803 A1 7/2003 Sequin et al.
2003/0187497 A1 10/2003 Boylan et al.
2004/0002753 A1 1/2004 Burgermeister et al.
2004/0006381 A1 1/2004 Sequin et al.
2004/0093077 A1 5/2004 White et al.
2004/0098080 A1 5/2004 Lau et al.
2004/0098091 A1 5/2004 Erbel et al.
2004/0167616 A1 8/2004 Camrud et al.
2004/0176837 A1 9/2004 Atladottir et al.
2004/0215312 A1 10/2004 Andreas
2004/0215331 A1 10/2004 Chew et al.
2004/0249446 A1 12/2004 Patel et al.
2005/0015136 A1 1/2005 Ikeuchi et al.
2005/0033399 A1 2/2005 Richter
2005/0038500 A1 2/2005 Boylan et al.
2005/0075716 A1 4/2005 Yan
2005/0096726 A1 5/2005 Sequin et al.
2005/0125052 A1 6/2005 Iwata et al.
2005/0182479 A1 8/2005 Bonsignore et al.
2005/0192663 A1 9/2005 Lau et al.
2005/0222671 A1 10/2005 Schaeffer et al.
2006/0004437 A1 1/2006 Jayaraman
2006/0015171 A1 1/2006 Armstrong
2006/0015172 A1 1/2006 Boyle et al.
2006/0015173 A1 1/2006 Clifford et al.
2006/0030931 A1 2/2006 Shanley
2006/0036315 A1 2/2006 Yadin et al.
2006/0060266 A1 3/2006 Bales et al.
2006/0064154 A1 3/2006 Bales et al.
2006/0064155 A1 3/2006 Bales et al.
2006/0069424 A1 3/2006 Acosta et al.
2006/0074480 A1 4/2006 Bales et al.
2006/0095123 A1 5/2006 Flanagan
2006/0111771 A1 5/2006 Ton et al.
2006/0122691 A1 6/2006 Richter
2006/0136037 A1 6/2006 DeBeer et al.
2007/0168019 A1 7/2007 Amplatz
2008/0215135 A1 9/2008 Seguin et al.

FOREIGN PATENT DOCUMENTS

CA 2 281 775 A1 6/2000
EP 1 034 751 A2 9/2000
EP 1 290 987 A2 3/2003
EP 1 512 380 A1 3/2005
EP 1 512 381 A2 3/2005
EP 1 523 959 A2 4/2005
EP 1 563 806 A1 8/2005
WO WO 01/76508 A2 10/2001
WO WO 03/047651 A2 6/2003
WO WO 03/055414 A1 7/2003
WO WO 2004/017865 A1 3/2004
WO WO 2005/094728 A1 10/2005
WO WO 2006/087621 A2 8/2006

FRANGIBLE BRIDGE STRUCTURE FOR A STENT, AND STENT INCLUDING SUCH BRIDGE STRUCTURES

This application claims priority to French Patent Application No. 07 00109 and U.S. Provisional Patent Application No. 60/880,418, the entire contents of each of which are hereby incorporated herein by reference.

The present invention concerns a frangible bridge structure for a stent, and the stent including such bridge structures. It also concerns a system for placing a stent in a bodily conduit, in particular in a vascular bifurcation.

As one knows, the term "stent" designates an expandable tubular element, intended to be inserted in a bodily conduit, in particular a vascular conduit, to reestablish the nominal diameter of this conduit. Documents US 2006/0036315 and WO 03/055414 illustrate existing stent structures.

It is known from Document U.S. Pat. No. 7,029,492 B1 to provide a stent structure comprising successive stent portions connected by frangible bridges. The breaking of one or several of these bridges, in a determined location of the stent, makes it possible to adapt the shape of said stent to the treatment to be performed, in particular to open the stent laterally in order to reduce inhibition of blood flow by a stent at a bifurcation. This break is made using a balloon introduced at a suitable position between two consecutive stent portions, said balloon being inflated to exert pressure on these two stent portions in opposite directions, thereby exerting longitudinal tension on the neighboring connection portion(s) until these connection portions break.

In particular, Document U.S. Pat. No. 7,029,492 B1 discloses a frangible structure comprising a rectilinear connection portion connecting two consecutive stent portions, wherein are arranged, in the vicinity of each other, and from each of the two opposite longitudinal edges of said connection portion, two U-shaped notches. Each of these notches extends over the majority of the width of the connection portion, such that it defines, with the opposite longitudinal edge of the connection portion, a thinner portion of material, and the two thinner portions of material define an intermediate portion between them. These thinner portions make it possible to grant a relative fragility to the connection portion in the longitudinal direction, such that the latter can be broken when longitudinal tension is exerted on it by a balloon.

This bridge structure does, however, have the significant drawback of presenting a risk of simultaneous breaking of the two thinner portions under the action of the balloon, and therefore releasing said intermediate portion inside the patient's body.

Moreover, the flexibility produced by this structure is not perfect with regard to the overall longitudinal flexibility of the stent said structure makes it possible to obtain.

Document No. EP 1 512 380 describes a stent comprising bridges having a waveform structure, which do not make it possible to resolve the abovementioned drawbacks. Document No. WO 2006/087621, the entire contents of which are hereby incorporated herein by reference, describes frangible bridges, but which also do not resolve these drawbacks.

The present invention aims to resolve drawbacks of stents according to the prior art.

According to embodiments of the invention, the structure of the bridge comprises three successive branches, a first branch that is connected to one of the stent portions which the bridge structure makes it possible to connect and a second branch that is connected to the other of the stent portions which the bridge structure makes it possible to connect, these first and second branches being connected, by two connecting portions, to a third intermediate branch, between said first and second branches, these three branches extending parallel to each other with the longitudinal direction of these branches preferably being oriented perpendicular to the longitudinal direction of the stent, and in immediate proximity to each other. According to other embodiments, these branches may also extend parallel to each other with the longitudinal direction of these branches being oriented in a direction non-perpendicular to the longitudinal direction of the stent, and in immediate proximity to each other.

These three branches, through the different connecting portions connecting them to each other and through the connections of said first and second branches to the corresponding stent portions, allow the bridge structure to have significant flexibility, favorable to obtaining the desired overall longitudinal flexibility for the stent. The bridge structure also has a resistance such that it does not break under the normal physiological stresses to which it is subjected after implantation. Additionally, the bridge structure does not break on radial expansion of the stent. However, although the bridge structure does not break under normal physiological stresses or on radial expansion, the bridge structure is breakable under very low pressure or forces exerted by a breaking device. Thus, there are minimal physiological effects and damage to vessels, as well as minimal stent deformation, during the breaking of the bridge structure.

When tension is exerted on this bridge structure by suitable means, for example by a balloon, in such a way as to cause this bridge structure to break, the three branches open in the form of a broken line, forming two successive Vs connected to each other, whereof the tip of one is turned from the side opposite the balloon and whereof the tip of the other is turned from the side of the balloon; it could be observed that the breakage occurs at the tip of one of the two Vs (essentially that whereof the tip is turned from the side opposite the balloon) without a break also taking place at the tip of the second V, starting at an angle between the branches in the vicinity of 45°.

The bridge structure according to embodiments of the invention thus also makes it possible to resolve the essential problem constituted by the risk of releasing a portion of the structure of a frangible bridge inside the patient's body.

It is probable that this result comes from the combination of bending and twisting stresses exerted on the material constituting the branches of the bridge, both directly by the surface of the balloon and indirectly by the stent portions deformed by inflation of said balloon, as well as the combination of the immediate proximity, before deployment, of the branches of the bridge structure, which creates marked tips to the two Vs formed by the tension exerted by the balloon.

Preferably, the connecting portions of the bridge structure are formed so as to have a lower breakage resistance than that of the branches. This conformation may comprise a smaller cross-section of these connecting portions relative to that of the branches, for example in the form of a smaller width of these connecting portions relative to the width of the branches, or in the form of one or several bores or notches arranged in these connecting portions. The smaller width of a connecting portion may in particular result from a slot arranged in said connecting portion, from one of the edges thereof, said slot being able in particular to be oblique relative to the longitudinal direction which the branches assume when the stent is in its non-deployed state.

Said intermediate branch may for example have a length of 0.38 mm; said first and second branches may for example each have a length of 0.23 mm.

In embodiments, the branches may have a trapezoid-shaped transverse cross-section, with the longest side of the trapezoid being located on the radially-external side of the stent. In exemplary embodiments, the longest side may have a length of 0.05 mm; the side parallel to the longest side may have a length of 0.0375 mm; the distance between these sides (i.e. the height of said trapezoid) may be equal to 0.15 mm. (In this specification, the term "trapezoid" is intended to encompass shapes having respectively slightly convex and concave surfaces that may arise when the branches are formed by cutting a pre-existing tube.)

Stents according to the invention comprise a plurality of frangible bridges having one or more of the aforementioned structures.

Such stents may comprise stent portions formed by a plurality of struts connected to each other, consecutively, at their ends, by curved areas, these stent portions thus also having, in the deployed state of the stent, a structure in the form of a zigzag.

Said frangible bridges are advantageously connected to the stent portions at all or part of said curved areas.

Through this connection at curved areas, the frangible bridges do not encroach upon the space occupied by the stent portions. Failing this, the stent portions should be longer, which would not be favorable to the desired characteristics for the stent.

Said curved areas may be connected to bridges at every one or two curved areas or more, for example at every three curved areas in a row.

The curved areas of one stent portion may be arranged so as to come longitudinally across from adjacent curved areas of an adjacent consecutive stent portion, or may be circumferentially offset relative to these adjacent curved portions.

Systems for placing a stent in a bodily conduit, in particular in a vascular bifurcation, which the invention also concerns, comprises:

- a stent as previously stated, and
- a breaking device, able to be engaged between two consecutive stent portions and able to exert tension on the bridge structures connecting these two stent portions, so as to achieve the breaking of all or part of these bridge structures.

Said a breaking device may preferably comprise a balloon.

The invention will be well-understood, and other characteristics and advantages thereof will appear, in reference to the appended diagrammatic drawings, illustrating, as non-limiting examples, several possible embodiments of the inventive frangible bridge structures and stents.

For simplification, the parts or elements of one embodiment which are found identically or similarly in another embodiment will be identified using the same numeric references and will not be described again.

Figure 1:
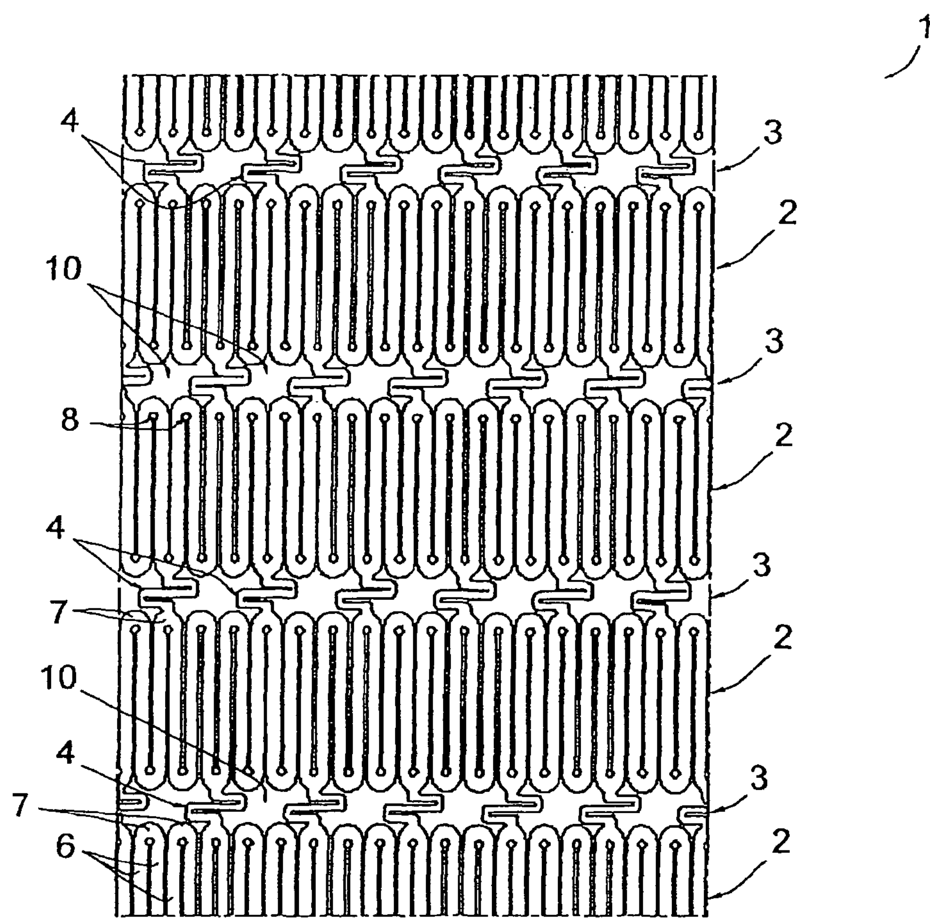
FIG. 1 is a partial developed view of a stent structure.
Figure 2:
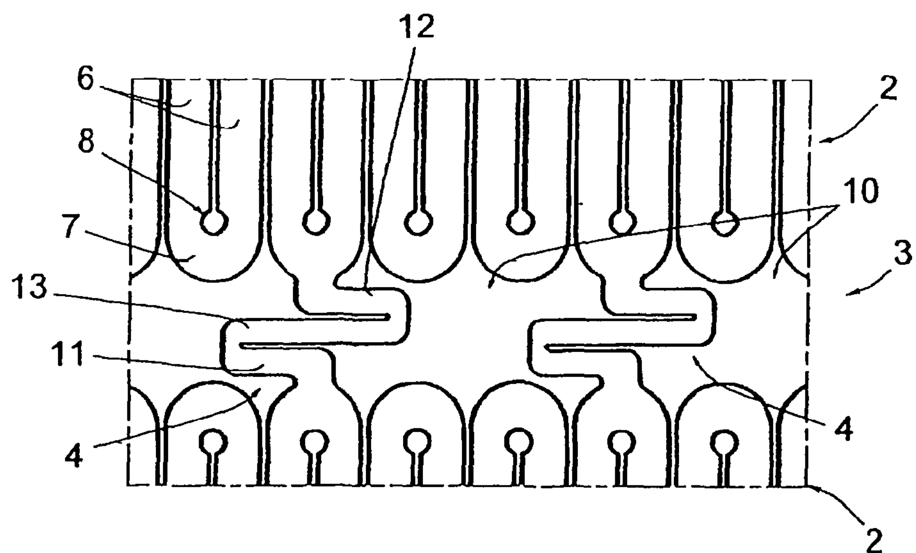
FIG. 2 is a partial view of this structure on an enlarged scale, at the level of the frangible bridges comprised by this structure.
Figure 3:
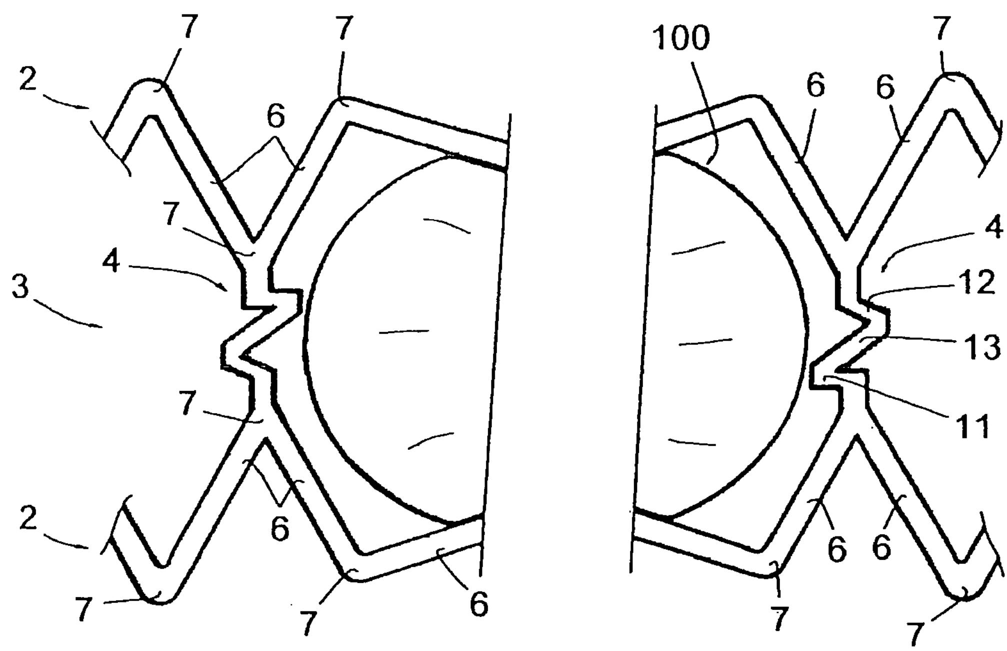
FIGS. 3 and 4 are partial views of this structure after deployment of the stent, before and after breaking of two frangible bridges using a balloon, respectively.
Figure 4:
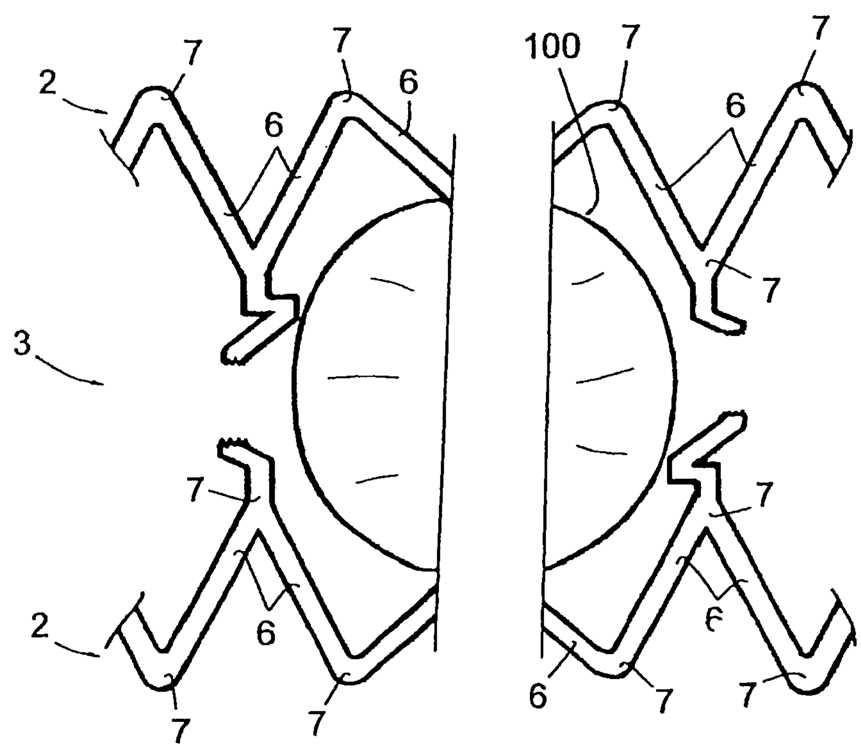

FIGS. 1 and 2 illustrate a stent structure 1 during manufacturing, and FIGS. 3 and 4 illustrate a portion of this structure after deployment.

The stent structure 1 may be obtained by cutting a cylinder of a nickel and titanium alloy known as "nitinol" using a laser. As shown in FIGS. 1 and 2, this cut is done so as to form successive stent portions 2 separated by transverse zones 3 comprising frangible bridges 4 which connect two successive stent portions 2.

As illustrated, each stent portion 2 may be formed by arranging two series of U-shaped slots, the U of each series being juxtaposed and the Us from one series being positioned inversely in relation to the Us of the other series, and are alternated and interlinked relative to those. Thus in each stent portion 2 is separated a plurality of struts 6 connected to each other, consecutively, at their ends, by curved areas 7. These stent portions 2 thus have, in the deployed state of the stent, a zigzag line structure, as visible in FIGS. 3 and 4.

Also, as shown in FIGS. 3 and 4, in the deployed state, there are no outwardly protruding peaks around the outer surface of the stent, nor do the branches 11 to 13 outwardly protrude. These features avoid perforation of a vessel wall.

The parallel struts of each slot of the embodiment of FIG. 1 end with circular cut-outs 8, making it possible to round the concave edge of the areas 7, thereby avoiding the risk of creating breakage beginnings at this edge.

At the zones 3, cut-outs 10 are arranged to separate the bridges 4. In this embodiment, each of said bridges 4 is connected to two areas 7 across from two consecutive stent portions 2, at every third area 7 of the same stent portion 2.

The cut-outs 10 are made so as to arrange, for each bridge structure 4, three successive branches, whereof a first branch 11 is connected to one of the areas 7 of the stent portion 2 which the bridge structure 4 makes it possible to connect and whereof a second branch 12 is connected to the area 7 of the other stent portion 2 which the bridge structure 4 makes it possible to connect; these first and second branches 11, 12 are connected, by two connecting portions, to a third branch 13, intermediate between said first and second branches 11, 12, these three branches 11 to 13 extending parallel to each other with the longitudinal direction of these branches 11 to 13 oriented perpendicular to the longitudinal direction of the stent. These three branches 11 to 13 are located in immediate proximity to each other, such that the two consecutive branches 11, 13 and 13, 12 are separated by a slot made by a laser beam, such that these two consecutive branches are separated from each other by a distance of less than a 100 microns, such as 5-50 microns, or preferably corresponding to the thickness of the laser beam, for example 15-25 microns, preferably about 15 microns. These branches 11 to 13 may alternatively extend parallel to each other with the longitudinal direction of these branches 11 to 13 being oriented in a direction that is not perpendicular to the longitudinal direction of the stent.

In the depicted embodiment, the intermediate branch 13 has a length of less than 500 microns, such as between 120 microns and 450 microns, but preferably 380 microns, and the first and second branches 11, 12 each have a length of less than 300 microns, such as between 25 microns and 250 microns, but preferably 230 microns. The width of each branch 11 to 13 is less than 100 microns, such as between 25 and 60 microns and preferably 50 microns; that of the connecting portions connecting these branches 11 to 13 two by two is 50 microns or less, such as between 15 and 50 microns, but preferably 25 microns.

Figure 9:
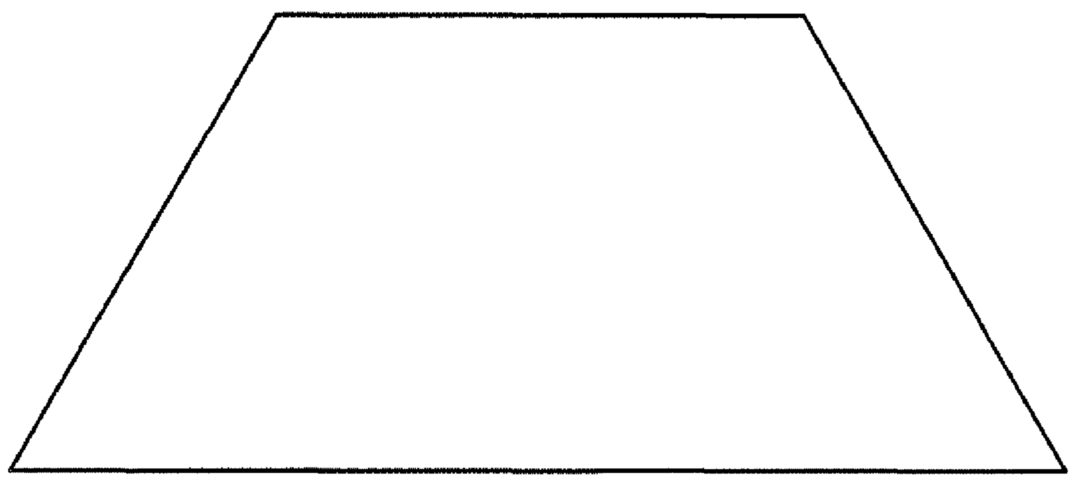
FIG. 9 is a view of a cross-section of a branch of an embodiment of a frangible bridge structure.

The branches 11 to 13 of this embodiment have a trapezoid-shaped transverse cross-section, as depicted in FIG. 9, with the longest side of this trapezoid located on the radially-external side of the stent. In the depicted embodiment, this longest side has a length of less than 100 microns, such as between 25 and 60 microns and preferably 50 microns; the side parallel to this longest side located radially on the internal side of the stent has a length of less than 100 microns, such as between 25 and 60 microns and preferably 37.5 microns; the distance between these sides (i.e. the height of said trapezoid) being less than 200 microns, such as between 80 and 200 microns, and preferably equal to 150 microns.

In practice, the stent may for example be used to treat a bifurcation comprising atheromatous plaques, which reduce the diameter of the vessels. A metallic guidewire is first introduced percutaneously through the main vessel then through one of the secondary vessels of the bifurcation to be treated, then a catheter is engaged in the main vessel and the secondary vessel while being guided by the guidewire, this catheter comprising the stent held in a radially contracted state by a sliding external sheath; when the distal end of the catheter is inside said secondary vessel, the sheath is slid backwards in a distal direction so as to release the stent, which deploys in this secondary vessel and then deploys in the main vessel, this deployment making it possible to support the wall of the vessel and therefore return these conduits of the bifurcation to suitable diameters.

As shown in FIGS. 3 and 4, during deployment of the stent, the stent portions 2 are radially expanded, assuming a zigzag line configuration. The three branches 11 to 13 of each bridge 4, the various connecting portions connecting these branches 11 to 13 to each other and the connections of said first and second branches 11, 12 to the corresponding stent portions 2, grant the bridge structure 4 significant flexibility, favorable to obtaining the desired overall longitudinal flexibility for the stent.

A second guidewire is introduced and is then engaged in the main vessel, then, through holes in the stent wall, into the other secondary vessel of the bifurcation. This second guidewire is advantageously passed through the hole closest to the carena, i.e. the area of the bifurcation corresponding to the beginning of the two secondary vessels. A catheter containing a balloon 100 is then introduced and engaged on the second guidewire until a portion, for example half, of the balloon 100 is engaged and extends through the wall of the stent.

The balloon 100 is then inflated, for example at a pressure of 4 to 18, preferably 4 to 10, atmospheres, and exerts, on the two stent portions 2 between which it is engaged, a tension separating these two portions from each other. This inflation causes twisting and stretching causing bending of the material of the bridges 4, until the bridges 4 located between these two stent portions 2 break, preferably with the exception of the bridge(s) 4 located diametrically opposite where the balloon went through, such that two separate but preferably connected tubular stent parts are thus formed, one extending in the main vessel and the other in the secondary vessel.

During inflation of the balloon 100, the three branches 11 to 13 unfold in the form of a zigzag line, forming two successive Vs connected to each other, whereof the tip of one is turned from the side opposite the balloon 100 and whereof the tip of the other is turned from the side of this balloon (cf. FIG. 3); it could be observed that with the bridge structure 4 described above, breaking takes place at the tip of one of the two Vs (essentially that whereof the tip is turned from the side opposite the balloon (100)) without a break also taking place at the tip of the second V (cf. FIG. 4).

The balloon is then deflated, and then the catheter is removed, followed by the removal of the guidewire.

Figure 5:
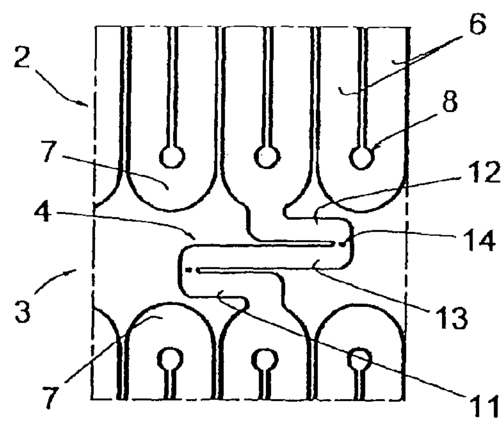
FIG. 5 is a view similar to FIG. 2, of another embodiment of a frangible bridge structure.
Figure 6:
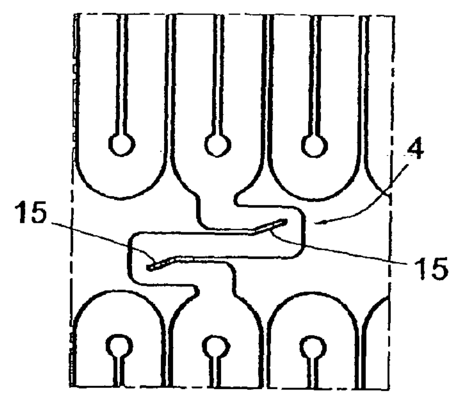
FIG. 6 is a view similar to FIG. 2, of another embodiment of a frangible bridge structure.

As stated above, the connecting portions connecting the branches 11 to 13 can have a smaller width than that of these branches so as to have a lower breakage resistance than that of the branches 11 to 13. FIG. 5 shows that, jointly or alternatively, these connecting portions may comprise holes 14 weakening their resistance; FIG. 6 shows that these connecting portions may alternatively (or also) have slots 15 arranged in them, from their inner edges, these slots 15 preferably being oblique in relation to the longitudinal direction of the branches 11 to 13 in the non-deployed state of the stent.

Figure 7:
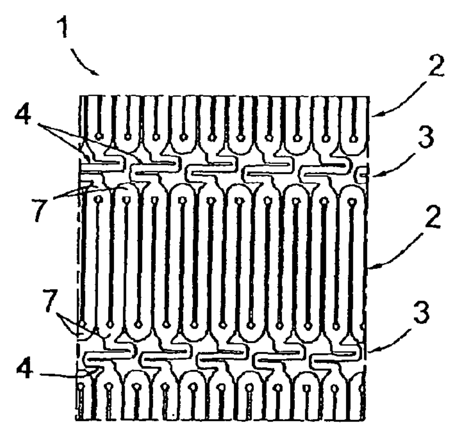
FIG. 7 is a view similar to FIG. 1 of another embodiment of a stent structure.

FIG. 7 shows that the curved areas 7 of the stent portions 2 may be connected to bridges 4 at every two curved areas.

Figure 8:
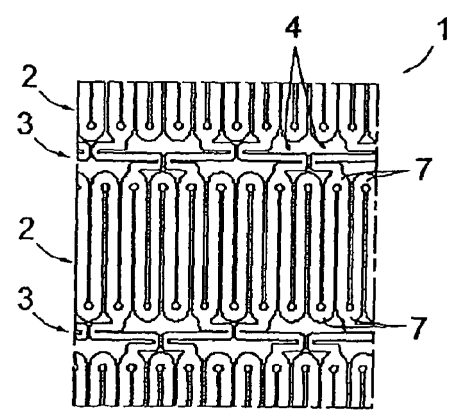
FIG. 8 is a view similar to FIG. 1 of another embodiment of a stent structure.

FIG. 8 shows that the bridges 4 may have inverse arrangements from one bridge 4 to a consecutive bridge 4 within a same zone 3, and that the curved areas 7 of one stent portion 2 may, independently or not of these inverse arrangements of the bridges 4, be offset relative to the curved areas 7 of the consecutive stent portion 2.

As shown by the preceding, the invention provides frangible bridge structures, stents including such bridge structures and methods for producing and using these bridge structures and stents, presenting inter alia the determining advantage of resolving an essential problem constituted by the risk of a portion of a frangible bridge structure being released in the patient's body.

It goes without saying that the invention is not limited to the embodiments described above as examples, but that it extends to all embodiments covered by the appended claims.

The invention claimed is:

1. A frangible bridge structure for a stent, comprising:

successive first, second and third branches, said first branch being connected to one of a plurality of stent portions that the frangible bridge structure allows to connect, said second branch being connected to a second of the plurality of stent portions that the frangible bridge structure allows to connect, said third branch being an intermediate branch that extends between said first and second branches, the first and second branches being connected, by two frangible connecting portions, to the third branch, the three branches extending parallel to each other and in immediate proximity to each other; wherein the connecting portions of the bridge structure are formed so as to have a lower breakage resistance than a breakage resistance of the branches.

2. The frangible bridge structure according to claim 1, wherein the branches extend parallel to each other such that the longitudinal direction of the branches is oriented perpendicular to a longitudinal direction of the stent in use.

3. The frangible bridge structure according to claim 1, wherein the branches extend parallel to each other such that a longitudinal direction of the branches is oriented non-perpendicular to a longitudinal direction of the stent in use.

4. The frangible bridge structure according to claim 1, wherein the bridge structure is breakable under a balloon inflation pressure of 4 to 10 atmospheres.

5. The frangible bridge structure according to claim 1, wherein the bridge structure is flexible with bending of the bridge structure while being frangible when longitudinal extension forces are applied to the bridge structure.

6. The frangible bridge structure according to claim 1, wherein the connecting portions of the bridge structure have a smaller cross-section than a cross-section of the branches, in the form of a smaller width of the connecting portions relative to the width of the branches, and/or in the form of one or several bores or notches arranged in the connecting portions.

7. The frangible bridge structure according to claim 6, wherein the smaller width of a connecting portion results from a slot in said connecting portion, extending from an edge of said connecting portion.

8. The frangible bridge structure according to claim 7, wherein said slot is oblique relative to the longitudinal direction of the branches when in a stent in a non-deployed state.

9. The frangible bridge structure according to claim 1, wherein consecutive said branches are separated from each other by a distance of less than 100 microns.

10. The frangible bridge structure according to claim 1, wherein the intermediate branch has a length of less than 500 microns.

11. The frangible bridge structure according to claim 1, wherein a width of each branch is less than 100 microns.

12. The frangible bridge structure according to claim 1, wherein a width of the connecting portions is 50 microns or less.

13. The frangible bridge structure according to claim 1, wherein the branches have a trapezoid-shaped transverse cross-section, with the longest side of the trapezoid being located on the radially-external side of a stent.

14. The frangible bridge structure according to claim 13, wherein the longest side of the trapezoid has a length of less than 100 microns; the side parallel to the longest side located radially on the internal side of the stent has a length of less than 100 microns; and the distance between these sides, i.e. the height of said trapezoid, is less than 200 microns.

15. A stent, comprising a plurality of frangible bridges having the bridge structure according to claim 1.

16. The stent according to claim 15, wherein the stent comprises stent portions formed by a plurality of struts connected to each other, consecutively, at their ends, by curved areas, the stent portions also having, in a deployed state of the stent, a zigzag structure.

17. The stent according to claim 16, wherein the connecting portions of the bridge structure have a lower breakage resistance than a breakage resistance of the struts.

18. The stent according to claim 17, wherein the branches remain parallel to a side wall of a portion of the stent to which they are attached after breakage at a connecting portion of the bridge structure.

19. The stent according to claim 16, wherein said frangible bridges are connected to the stent at all or part of said curved areas.

20. The stent according to claim 16, wherein said curved areas are connected to said bridges at every two or more curved areas.

21. The stent according to claim 15, wherein the bridge structure is breakable under a balloon inflation pressure of 4 to 10 atmospheres.

22. A system for placing a stent in a bodily conduit, such as a vascular bifurcation, the system comprising:

- a stent according to claim 15, and
- a breaking device configured to be engaged between two consecutive stent portions and to exert tension on the bridge structures connecting the two stent portions, so as to achieve breaking of all or part of these bridge structures.

23. The system according to claim 22, wherein said breaking device comprises a balloon.

24. A method of treating a bodily conduit, the method comprising:

- introducing a stent according to claim 15, in a radially contracted state into a main vessel and a first branch vessel of said bodily conduit; allowing the stent to self-expand; introducing a balloon through the main vessel, through a wall of the stent and then through a second branch vessel of said bodily conduit; inflating the balloon such that the balloon causes the stent to break into two stent parts; and removing the balloon from the vessels.

25. The method according to claim 24, wherein the balloon is passed through a slot in the wall of the stent closest to a carena of the vessels.

26. The method according to claim 24, wherein the balloon is inflated at a pressure of 4 to 10 atmospheres to cause the stent to break.

27. The frangible bridge structure according to claim 1, wherein the frangible bridge structure is configured to be broken by a breaking device and not under physiological stress.

28. The frangible bridge structure according to claim 1, wherein the frangible bridge structure is configured to be broken inside a bodily conduit with minimal physiological effects and damage to the conduit, and minimal stent deformation, during breaking of the bridge structure.

29. The frangible bridge structure according to claim 28, wherein the frangible bridge structure is configured to be broken inside the conduit by expansion of a balloon adjacent a said connecting portion and substantially perpendicular to a curved surface defined by said branches.

30. The frangible bridge structure according to claim 1, wherein consecutive said branches are separated from each other by a distance of less than 50 microns.

31. The frangible bridge structure according to claim 1, wherein consecutive said branches are separated from each other by a distance of 5-25 microns.

32. The frangible bridge structure according to claim 1, wherein a width of each branch is greater than a width of a space of separation between consecutive said branches.

33. The frangible bridge structure according to claim 1, wherein the structure has the first and second branches connected, by the two frangible connecting portions, to the third branch, the three branches extending parallel to each other and in immediate proximity to each other, prior to use.

* * * * *